US008685378B2

(12) United States Patent
Dissard et al.

(10) Patent No.: US 8,685,378 B2
(45) Date of Patent: Apr. 1, 2014

(54) COMPOSITION FOR TISSUE PRESERVATION

(75) Inventors: Dominique Dissard, Entrance (FR); Jean-Charles Jay, Monsteroux Milieu (FR); Denis Gilotin, Mions (FR); Henri Graugnard, Le Paradou (FR); Nabil Berka, Lyons (FR)

(73) Assignee: OGF, Paris (FR)

( * ) Notice: Subject to any disclaimer, the term of this patent is extended or adjusted under 35 U.S.C. 154(b) by 448 days.

(21) Appl. No.: 12/922,264

(22) PCT Filed: Mar. 11, 2009

(86) PCT No.: PCT/FR2009/050399
§ 371 (c)(1),
(2), (4) Date: Dec. 21, 2010

(87) PCT Pub. No.: WO2009/122056
PCT Pub. Date: Oct. 8, 2009

(65) Prior Publication Data
US 2011/0097295 A1   Apr. 28, 2011

(30) Foreign Application Priority Data

Mar. 13, 2008  (FR) ...................................... 08 51637

(51) Int. Cl.
*A01N 1/00*    (2006.01)
(52) U.S. Cl.
USPC ........................................................... 424/75

(58) Field of Classification Search
None
See application file for complete search history.

(56) References Cited

U.S. PATENT DOCUMENTS

| | | |
|---|---|---|
| 5,196,182 A | 3/1993 | Ryan |
| 5,260,048 A | 11/1993 | Ryan |
| 5,459,073 A | 10/1995 | Ryan |
| 5,460,797 A | 10/1995 | Ryan |
| 5,811,099 A | 9/1998 | Ryan |
| 5,849,517 A | 12/1998 | Ryan |
| 5,977,153 A | 11/1999 | Camiener |
| 2002/0066168 A1 | 6/2002 | Barrow |
| 2003/0206884 A1 | 11/2003 | Barrow |

FOREIGN PATENT DOCUMENTS

WO   WO 2006/059126   6/2006

OTHER PUBLICATIONS

International Search Report for PCT/FR2009/050399, published 2009.

*Primary Examiner* — James H. Alstrum-Acevedo
*Assistant Examiner* — Monica Shin
(74) *Attorney, Agent, or Firm* — B. Aaron Schulman, Esq.; Stites & Harbison, PLLC

(57) ABSTRACT

The present invention relates to the use of a composition comprising 2-bromo-2-nitropropane-1,3-diol for tissue preservation and more particularly for the preservation of bodies and anatomical parts or for carrying out embalming procedures.

11 Claims, No Drawings

COMPOSITION FOR TISSUE PRESERVATION

The present invention relates to a novel composition for tissue preservation, in particular for the preservation of anatomical parts or for carrying out embalming procedures.

The preservation of biological samples and the embalming of human or animal bodies have historically been performed using fluids containing significant amounts of formaldehyde.

However, formaldehyde has a large number of drawbacks as a preservative. For example, there are many sanitary and environmental risks associated with its use particularly due to its high toxicity. Among the dangers of short-term exposure to formaldehyde may be cited nose and throat irritations, headaches and nausea. Long-term exposure may cause chronic deterioration in lung function, skin inflammation and cancer.

Formaldehyde also dehydrates biological tissue and has a noxious odour. A drawback of the use of formaldehyde in embalming fluids is linked to the fact that formaldehyde coagulates and reticulates many bodily fluids which causes stiffening of body tissue. Consequently, it may be difficult and time-consuming to ensure even distribution of the embalming fluid throughout the body. Drying of the skin by formaldehyde may also lead to grazing on the body and localised burns. Owing to its volatile nature, formaldehyde has low residual effectiveness, which leads to rapid decomposition of the skin surfaces.

Formaldehyde therefore presents various sanitary, hygiene and safety problems.

At present, there is no satisfactory substitute product.

The object of the present invention is therefore to provide a product for tissue preservation, and in particular for carrying out embalming procedures, which overcomes the above-mentioned drawbacks linked to the use of formaldehyde.

More particularly, said product should on the one hand ensure satisfactory presentation of the deceased to facilitate the grieving process for families and on the other hand preserve the body for a sufficiently long period, making it possible to carry out the operations laid down by the public authorities and requiring the use of preservation procedures.

Another object of the present invention is to provide a novel composition for tissue preservation which provides the personnel carrying out the procedures and more generally any person frequenting the premises where the procedures have been carried out, or who is simply close to the body of the deceased, with satisfactory sanitary, hygiene and safety conditions which do not present any particular danger.

The present invention relates to the use of a composition comprising 2-bromo-2-nitropropane-1,3-diol for tissue preservation.

Bronopol or 2-bromo-2-nitropropane-1,3-diol ($C_3H_6BrNO_4$) is a crystalline powder of which the colour varies from white to pale yellow.

The product is stable and is used as a bactericide.

Bronopol is a biocide which presents little or no risk to human health. Its use prevents vapour inhalation when the procedures are carried out by the practitioner. Moreover, bronopol is not volatile at room temperature.

According to a particular embodiment, the above-mentioned composition is used for the preservation of human anatomical parts, in particular for the preservation of bodies for dissection.

According to another particular embodiment, the above-mentioned composition is used to carry out embalming procedures.

The term "embalming procedures" refers to procedures for the preservation and presentation of the body of a deceased person, specifically embalming techniques or techniques relating to the embalming of cadavers.

The above-mentioned composition may therefore be used for embalming procedures, for the preservation of bodies with a view to their dissection and for the preservation of human and animal anatomical parts.

The present invention relates in particular to the use as defined above of a composition comprising at least about 1% by weight of 2-bromo-2-nitropropane-1,3-diol.

Attention is drawn here to the fact that the percentages by weight indicated above and in the rest of this document are expressed in relation to the total weight of the composition according to the invention.

Preferably, for the use as defined above, the above-mentioned composition comprises from about 0.5% to about 2.5%, and preferably from about 0.8% to about 2.5% by weight of 2-bromo-2-nitropropane-1,3-diol.

These concentration values are linked to the variability of the bronopol reaction depending on the specific state of the bodies treated.

According to a particular embodiment, the present invention relates to the use of a composition comprising 2-bromo-2-nitropropane-1,3-diol for tissue preservation, characterised in that said composition comprises from 0.1% to 8% by weight of 2-bromo-2-nitropropane-1,3-diol.

More particularly, the present invention also relates to the use for embalming procedures of a composition comprising from 0.4% to 8% by weight of 2-bromo-2-nitropropane-1,3-diol.

According to a particular embodiment, the present invention relates to the use for embalming procedures by arterial injection of a composition comprising from 0.3% to 2.4%, preferably from 0.3% to 1.2%, advantageously from 0.3% to 0.6%, from 0.4% to 0.6%, and most preferably 0.6% by weight of 2-bromo-2-nitropropane-1,3-diol.

According to a particular embodiment, the present invention relates to the use for thanatalogical procedures by cavity injection of a composition comprising from 2% to 8%, preferably from 2.5% to 5%, and most preferably 5%, by weight of 2-bromo-2-nitropropane-1,3-diol.

According to another embodiment, the present invention relates to the use for embalming bodies for dissection of a composition comprising from 0.8% to 1.2% by weight of 2-bromo-2-nitropropane-1,3-diol.

According to another embodiment, the present invention relates to the use for organ preservation of a composition comprising from 0.1% to 0.5%, preferably 0.15%, by weight of 2-bromo-2-nitropropane-1,3-diol.

In general, the above-mentioned compositions are either solutions packaged for transport, which are then diluted before injection, or solutions ready for injection.

According to another embodiment, for the use described above, the above-mentioned composition also comprises an anticoagulant, preferably sodium citrate.

An anticoagulant is a molecule for preventing or delaying blood coagulation. In the context of the composition according to the invention, the anticoagulant dissolves blood clots and promotes the flow of said composition in the arteries and arterial drainage.

Among anticoagulants may be cited sodium citrate, heparin, sodium oxalate, EDTA, borates such as sodium borate, sodium tetraborate or sodium pyroborate, magnesium sulphate, sodium chloride, sodium sulphate and sodium phosphate.

It will be noted that some of these products are used in medicine for thinning the blood. For example, heparin and sodium citrate may be used to facilitate blood flow and prevent the formation of blood clots in patients, and magnesium sulphate may be used in embalming fluids to promote the drainage of water contained in oedemas.

More particularly, in the context of the present invention, the above-mentioned composition comprises from about 0.05% to about 2%, preferably from about 0.1% to about 1.5%, by weight of anticoagulant, and in particular from about 0.1% to about 1.5% by weight of sodium citrate.

For procedures carried out on bodies intended for dissection which cannot be punctured or drained, a low concentration of the coagulant substance is used. This also applies for deceased persons whose religious faith forbids puncturing.

Moreover, in some conditions, this concentration will be increased to improve cardiac puncture.

The present invention also relates to the use as described above, characterised in that the above-mentioned composition also comprises a penetrating agent, in particular glycerine.

In the context of the present invention, the penetrating agent transports the fluids by drainage and capillary action and is also associated with a dehydrating effect.

Among the penetrating agents may be cited sorbitol, ethylene glycol and propylene glycol.

More particularly, for the present invention, the above-mentioned composition comprises from about 3% to about 40% by weight of penetrating agent, in particular from about 3% to about 40% by weight of glycerine.

The present invention also relates to the use as described above, characterised in that the above-mentioned composition also comprises an antiseptic or solvent, in particular chosen from methanol and ethanol.

An antiseptic is a substance that disinfects and kills microbial germs. For the present invention, preferably ethanol and methanol are used. These products have antiseptic, preservative and dehydrating properties; they act as solvents of the products present in the composition according to the invention.

Preferably, the antiseptic used is a primary monoalcohol of low molar mass, allowing effective diffusion in the tissue.

More particularly, in the context of the present invention, the above-mentioned composition comprises from about 2% to about 45%, preferably from about 2% to about 40%, and most preferably from about 2% to about 35% by weight of antiseptic, and in particular from about 2% to about 35% by weight of methanol or ethanol.

The present invention also relates to the use as described above, characterised in that the above-mentioned composition also comprises a colouring, in particular chosen from amaranth and eosin.

Accordingly, the composition used for the present invention also contains a tissue colouring. Among the colourings used, apart from amaranth (which gives a pinkish red colour) and eosin (which gives a pink colour), may be cited ponceau (which gives a cherry red colour), erythrosine (which gives a cherry red colour) and carminic acid (which gives a carmine red colour).

These colourings are inert, that is, they simply pigment the composition according to the invention, and these products are classified by colour range depending on the subjects encountered.

More particularly, for the present invention, the above-mentioned composition comprises less than about 0.2% by weight of colouring, in particular from 0 to 0.2% by weight of amaranth or eosin.

Other products may be introduced into said composition in variable amounts to obtain the expected results, depending on the different application circumstances, such as jaundice for example.

Thus, if there is an excess of unconjugated bilirubin in the tissue, it is possible to add glucuronic acid and a specific enzyme, diphosphate uridyltransferase, to the composition, which makes the bilirubin and hence the yellow or greenish colour disappear.

The present invention also relates to a composition comprising 2-bromo-2-nitropropane-1,3-diol, an anticoagulant, a penetrating agent, an antiseptic and, if necessary, a colouring.

Preferably, the above-mentioned composition is composed of 2-bromo-2-nitropropane-1,3-diol, an anticoagulant such as sodium citrate, a penetrating agent such as glycerine, an antiseptic such as methanol or ethanol, and a colouring such as eosin or amaranth.

According to an advantageous embodiment, the composition comprises:
from about 0.5% to about 2.5% by weight of 2-bromo-2-nitropropane-1,3-diol;
from about 0.1% to about 2% by weight of anticoagulant;
from about 3% to about 40% by weight of penetrating agent;
from about 2% to about 45% by weight of antiseptic; and
less than about 0.2% by weight of colouring.

The present invention also relates to an embalming method which comprises the injection into the body to be embalmed of a composition as described above comprising 2-bromo-2-nitropropane-1,3-diol. Injection may be made into the cavities, in particular the thoracic or abdominal cavities, or into the arteries, in particular the femoral, carotid or axillary arteries.

An advantageous composition according to the invention comprises 2-bromo-2-nitropropane-1,3-diol and an antiseptic, in particular chosen from methanol and ethanol, said composition being characterised in that it comprises from 4% to 8%, preferably from 5% to 8%, and most preferably from 5% to 7.2% by weight of 2-bromo-2-nitropropane-1,3-diol.

This composition may also comprise an anticoagulant, a penetrating agent and, if necessary, a colouring.

An advantageous composition according to the invention comprises 2-bromo-2-nitropropane-1,3-diol, an anticoagulant, a penetrating agent, an antiseptic and if necessary a colouring, said composition being characterised in that it comprises from 0.3% to 2.4%, and preferably from 0.3% to 1.2% by weight of 2-bromo-2-nitropropane-1,3-diol. This composition is intended in particular for use in arterial injection.

Another advantageous composition according to the invention comprises 2-bromo-2-nitropropane-1,3-diol, an antiseptic and if necessary a colouring, said composition being characterised in that it comprises from 2% to 8%, preferably from 2.5% to 5%, and most preferably 5%, by weight of 2-bromo-2-nitropropane-1,3-diol. This composition is intended in particular for use in cavity injection.

Another advantageous composition according to the invention comprises 2-bromo-2-nitropropane-1,3-diol, an anticoagulant, a penetrating agent, an antiseptic and if necessary a colouring, said composition being characterised in that it comprises from 0.8% to 1.2% by weight of 2-bromo-2-nitropropane-1,3-diol. This composition is intended in particular for use in embalming bodies for dissection.

Another advantageous composition according to the invention comprises 2-bromo-2-nitropropane-1,3-diol, an anticoagulant, a penetrating agent, an antiseptic and if necessary a colouring, said composition being characterised in that it comprises from 0.1% to 0.5%, preferably 0.15%, by weight of 2-bromo-2-nitropropane-1,3-diol. This composition is intended in particular for use in organ preservation.

As indicated above, the preferred bronopol concentration in ready-to-inject compositions for arterial injection is 0.6% by weight, whereas the preferred bronopol concentration in ready-to-inject compositions for cavity injection is 5% by weight. These optimal concentrations have been determined by the applicant in the light of numerous experimental tests.

Thus, analysis of all the test results shows that with regard to the bronopol concentration, too high a concentration generally leads to negative, corresponding phenomena in particular:

a risk of premature drying of the body, particularly of the visible parts which are the face and hands;
a reduction in the suppleness of the skin and tissue;
a deterioration in the colour of the face and hands;
the probable appearance initially of red marks followed by brownish marks which are unsightly and therefore detrimental to the presentation of the deceased.

On the other hand, too low a concentration may have the opposite effect and not sufficiently hinder decomposition of the body.

The tests carried out with the target concentration also show that:

presentation of the deceased persons is good,
the colour is natural,
the suppleness of the skin and tissue is preserved,
there is no gaseous swelling in the region of the abdomen during normal display (in particular six to eight days),
there is no odour of decomposition or of chemical products for example.

The applicant has also carried out additional tests to assess the subsequent decomposition of the body after burial. It is important to stress that, in embalming procedures carried out for the presentation and preservation of deceased persons who are shown to their friends and family, the object is not to "mummify" the bodies but simply to maintain good preservation hygiene and a good quality of visual presentation during the legally required period or periods before the body "disappears", in order to facilitate the grieving process.

Moreover, the town planning problems in particular concerning cemetery management (the need to renew concessions at regular intervals) lead to the view that, although embalming procedures must temporarily halt decomposition of the body, they must also allow decomposition to resume subsequently.

In this regard it is important to make clear that, in all the bacteriological analyses carried out on embalmings using the target concentrations of injection products (0.6% for the arterial product and 5% for the cavity product), the presence of bacteria was observed in the body fluid.

This means that the use of the stabilised products (with the target composition) does not completely arrest bacteriological growth and does not completely halt the process of body decomposition, which subsequently resumes.

The results obtained according to the bronopol concentration were as follows:

| Bronopol concentration | Presence of bacteria in the body fluid |
|---|---|
| ≥1.2% | 1 out of 3 cases with bacteria |
| 0.90% | 1 out of 2 cases with bacteria |
| ≤0.80% | 7 out of 8 cases with bacteria |

The impact of the bronopol concentration on the presence of bacteria in the body fluid and hence potentially on the future decomposition of the body after burial is therefore clear.

However, it is important to state that bronopol degradation over time must, in parallel with a reduction in the biocidal effect of the active substance, correspond to the reappearance of bacteria even in cases where these are almost absent in the short term owing to too high a bronopol concentration.

Such cases, in which the concentrations are higher than 1%, relate only to embalmings for dissection and are less important insofar as the anatomical parts resulting from this type of embalming are systematically cremated.

With regard to cavity injection, the systematic absence of gas in the abdominal region leads to the conclusion that the cavity product is effective.

As indicated above, the preferred bronopol concentration in ready-to-inject compositions used in embalming for dissection is between 0.6% and 1.2% bronopol. These optimal concentrations have been determined by the applicant in the light of numerous experimental tests.

In this type of procedure, no liquid tapping or cavity injection is carried out. The product must therefore be substantially more active than the arterial liquid used for conventional embalming.

Tests conducted at 2.4% then at 1.5% then at 1.2% then at 1% then at 0.8% showed optimal achievement of the required objectives with a concentration of between 0.8% and 1.2%.

The results of the dissections carried out on the bodies show that, whatever the concentration above 0.8% (most typically approximately 1%), the characteristics of the body are as follows:

good tissue suppleness,
satisfactory pink colour,
consistency close to normal (before death),
dissection easily performed,
lack of odour emanating from the deep tissue,
lack of tissue fibrosis, and
muscles not particularly friable (no weakening).

In conclusion, whether the embalmings are of deceased persons for presentation to their families or for dissection, the results fully meet quality expectations.

With regard more particularly to embalmings for the presentation of the deceased, when compared with procedures carried out with formaldehyde-based products, the following points in favour of using the compositions according to the invention are noted:

Preservation: satisfactory and substantially identical to the results obtained with formaldehyde and in all cases broadly sufficient in the context of preservation procedures for the presentation of bodies to families or for carrying out dissections.

Presentation of the body:
Better colour than with formaldehyde,
Much improved natural appearance,
Much improved suppleness of the skin and tissue as a result of good rehydration, and
Total lack of odour.

Overall, the preservation aspect is identical and the appearance is considerably better than if formaldehyde is used.

For embalming for dissection and similar reasons, the practitioners who carried out dissections with the compositions according to the invention considered these products far superior to formaldehyde-based products. In fact, formaldehyde-based products lead to very rapid and significant dehydration which, by making the skin and tissue very hard, make it difficult to carry out dissection in satisfactory conditions.

Moreover, the odours released by formaldehyde-based products are difficult to tolerate.

Although the weakest possible concentrations are chosen because there is a wish not to "burn" the body by too aggressive a solution, these concentrations have been carefully developed so as to have the minimum impact on the environment, given the small amounts of bronopol used.

By definition, a biocide is a substance that is harmful to life and hence the environment. To limit as far as possible any impact on the environment, it is therefore vital to determine the lowest possible bronopol concentrations to achieve the desired preservation and presentation results on the one hand, but also the least possible environmental impact.

In this regard, the studies carried out by the applicant lead to the conclusion that, for bodies that disappear through cremation or burial, the concentrations used do not present a danger to the environment.

Moreover, and in the context of burial and cemetery management, it is important that decomposition of the body is not halted but only slowed down.

The low bronopol concentrations used show a persistence, not an arrest, of bacteriological activity, which suggests that, for bronopol concentrations of less than 0.8% in diluted solution for arterial injection, decomposition of the body is certainly slowed down for a period but that it then resumes, thus allowing decomposition of the body to begin again.

EXPERIMENTAL SECTION

I—Arterial Infection

To prepare the composition according to the invention, 1 liter of solution is prepared which is then diluted with 2 to 8 additional liters of water.

The composition by mass is as follows:
sodium citrate: from 2 to 15 g;
glycerine: from 30 to 400 g;
ethanol or methanol: from 20 to 350 g;
amaranth or eosin: from 0 to 2.0 g;
bronopol: more than 10 grams;
water 1) Preparation of the Arterial Solution Before Injection:
Two methods are possible, namely:
either the concentrated solution is ready for use and in this case all that is needed is to add the desired additional volume of water (from 2 to 8, or up to 12 liters of additional water);
or the concentrated solution is prepared without having introduced bronopol; thus, after introducing bronopol in the concentrated solution, the desired additional volume of water should be added.

It is important to mention that the amount of water added, usually approximately 5 liters (or as much as 11 liters) to 1 liter of base solution, may be modified depending on the conditions observed at the time of injection. The state of the deceased and the causes of death may lead to different concentrations.

For arterial injection, the following compositions were prepared and tested (these compositions are prepared for 1 liter of concentrated solution to which 5 liters of water are added):
(1) composition containing 0.8% by weight of bronopol, which comprises:
49.8 g of bronopol;
9 g of citrate;
301.37 g of glycerine;
254.40 g (at 95%) of alcohol; and
4 drops of eosin.

(2) composition containing 1.7% by weight of bronopol, which comprises:
100 g of bronopol;
5.5 g of citrate;
305 g of glycerine;
242 g (at 95%) of alcohol; and
4 drops of eosin.

(3) composition containing 1.2% by weight of bronopol, which comprises:
72 g of bronopol;
9 g of citrate;
305 g of glycerine;
242 g (at 95%) of alcohol; and
4 drops of eosin.

It should be noted that, for persons of very large build, more solution will have to be injected to obtain higher injection volumes. This preparation can be adapted to the morphology of the case being treated. If the person has been kept in a refrigerated environment or if there has been a delay in injection following death, the concentrations will have to be adjusted to obtain optimal quality results.

2) Injection Method:
This operation uses the method generally used for embalming procedures, namely injection and drainage, said drainage being generally performed in the region of the right heart.

Injection is carried out through the femoral, carotid or axillary arteries.

The amount of fluid injected is approximately 6 liters, but this amount may vary depending on the state of the deceased and the diagnosis made by the embalmer, for example the need for more drainage.

Additional tests were carried out.

Accordingly, the following concentrated product, before dilution for injection, was prepared (composition 3'):
Bronopol: 72 grams
Glycerine: 300 grams
Methanol or ethanol: 240 grams
Sodium citrate: 9 grams
Eosin: a few drops
Water: enough to make 1 liter.

It should be noted that the means of varying the bronopol concentration are as follows:

1—either the standard solution of the concentrated product with 72 g of bronopol is retained and enough water for dilution is added to adjust the final bronopol concentration (this means that the concentration of the other constituents may have to be changed depending on the amount of water added for dilution);

2—or the bronopol content is adjusted in the concentrated solution which still comprises the same concentrations of the other components (apart from water, the quantity of which is adjusted to produce a liter); in this case, and in the standard solution above, the bronopol content may vary from 36 g to 144 g; the bronopol concentration therefore increases, for the same additional dilution (11 liters of water for 1 liter of concentrated solution, which is enough for two procedures each of 6 liters of diluted solution), from 0.3% to 1.2% bronopol with no change in the concentration (apart from the water) of the other components (a particular application of this example is a bronopol content of 48 g to obtain a diluted solution of 0.4% bronopol);

3—or an intermediate solution between the two previous methods is used which consists in varying the content of the different components correlatively to obtain the selected target bronopol content (from 0.3% to 1.2%) and intermediate concentrations of the other components in the diluted solution compared with that obtained in each of the two previous methods.

Next, the product to be injected is prepared from the above-mentioned concentrated product by dilution.

Accordingly, a product is prepared with a bronopol concentration of 0.6% by diluting 1 liter of concentrated solution with 11 liters of water (in the knowledge that 6 liters of dilution solution are required per procedure).

The composition per liter of the diluted ready-to-use solution (composition 3a) is therefore:
Bronopol: 6 grams (0.6%)
Glycerine: 25 grams (2.5%)
Methanol or ethanol: 20 grams (2%)
Sodium citrate: 0.75 grams per liter
Eosin: a few drops
Water: enough to make up 1 liter II—Cavity Injection In the case of cavity injection (a zone which does not affect the physical presentation of the body), the object sought is to halt bacterial proliferation. Therefore only products that have an antibacterial action should be used, specifically bronopol and methanol or ethanol. Thus, in this embodiment, the use of glycerine and citrate is not mandatory. However, provision may be made for the possible use of citrate, for example.

With regard to the concentrations and to increase the antibacterial effect, the bronopol and ethanol concentration is increased (see below) to a level of 5% bronopol and 40% of ethyl alcohol.

To prepare the composition according to the invention, 0.5 liters of solution is prepared of which the composition by mass is as follows:
bronopol: more than 10 g;
ethanol or methanol: more than 100 g;
water
1) Preparation of the Solution:
   Three methods may be considered, specifically:
   either the solution is ready for use;
   or the solution is a concentrated solution to which the necessary amount of water should be added;
   or bronopol is added before the procedure is carried out and the necessary water is added.
   For cavity injection, the following compositions were prepared and tested (these compositions are prepared for 500 ml and used as they are):
   (4) composition comprising:
   40 g of bronopol (8%); and
   257.31 g (at 95%) of alcohol.
   (5) composition comprising:
   25 g of bronopol (5%); and
   202 g (at 95%) of alcohol.
2) Injection Method:
   This operation uses the method widely practised in embalming procedures, that is, gas and fluid tapping in the region of the thoracic and abdominal cavities, and injection of the composition according to the invention into each of the cavities so that said composition is diffused optimally throughout the cavities concerned.
   Additional tests were carried out.
   Accordingly, the following product was prepared:
Bronopol: 50 grams
Methanol or ethanol: 400 grams
Water: enough to make up 1 liter (This solution is enough for two procedures, knowing that for each procedure 0.5 liters of pure (undiluted) solution are injected in the cavities).

The concentration of bronopol in the liquid is therefore 5%. Cavity injection is carried out using a solution that does not require dilution prior to injection.

III—Duration of the Procedure

The operating method for carrying out the procedure is identical to that used for a formaldehyde-based product. The duration of the entire procedure is identical, that is between 1 hour 15 minutes and 1 hour 30 minutes (including make-up).

IV—Results

Still using an identical base of glycerine, ethanol or methanol, tests were carried out using the compositions described in the examples above (compositions (1), (2), (3) and (3a) for arterial injection and compositions (4) and (5) for cavity injection).

As bronopol is one of the essential active ingredients in tissue preservation, varying it has a powerful influence on said preservation. The higher the concentration, the greater the preservation effect, but this may produce unwelcome factors with regard to the presentation of the bodies of the deceased.

The choice of concentration is therefore the result of a suitable compromise between the two objects sought (preservation and presentation), the optimum for both objects (for bodies that do not have any special characteristic) having been determined as 0.6%.

In the tests carried out, the bodies were observed for a maximum of fifteen days.

The object of varying the bronopol concentration is to establish the optimum concentration to achieve satisfactory preservation of the body and good presentation without too much dehydration.

The tests carried out on bodies that had no particular abnormality showed that a concentration of 0.6% bronopol led to satisfactory results.
1) Preservation of the Body:
   For cavity injection or arterial injection, a significant reduction in the decomposition of the body was observed in that:
   there was little change in the appearance of the deceased throughout the observation period;
   no gas appeared in the region of the cavities; and
   no particular odour was present during the observation period.
2) Appearance of the Deceased:
   After carrying out the procedure, rehydration of the tissue was observed, accompanied by good diffusion (fluidity) of the product according to the invention in the body. This was characterised by a more supple feel to the skin and a "softer" appearance. The deceased retained a natural appearance and did not have the waxy appearance often observed with injection using formalin products.
   The effects of bronopol are therefore satisfactory with regard to both preservation and the presentation quality of the deceased.
   The lack of decomposition, probably resulting from low bacterial growth, leads to the conclusion that sanitisation of the treated bodies is good.

V—Comparison Between the Product and Formalin

The operational method for the procedure is identical to that used for formalin products.

Regarding preservation of the bodies as such (over the observation period which was approximately fifteen days), it may be concluded that the effectiveness of the bronopol-based solutions and the formaldehyde-based solutions is identical. The essential difference lies in the appearance of the body which, as stated earlier, is more supple, with less degraded colour and thus a generally more "serene" and relaxed appearance than is the case when a formaldehyde solution is used.

As for solutions comprising formalin, the concentration of the product can be adjusted according to the nature of the bodies to be treated.

Therefore:
higher concentrations will be chosen for bodies with more advanced biological decomposition (that is, from approximately 0.8 to 1.2% by weight of bronopol);
concentrations of from 0.4 to 0.8% will be chosen for "normal" bodies so as not to cause too rapid a drying of the tissue;
for icterus (jaundice), the bronopol concentration may be further reduced to between 0.3 and 0.4%, which prevents the body from turning green and assists product diffusion in the tissue.

VI—Preservation of Anatomical Parts

1. Tests were also carried out within the faculty of medicine in the context of the preservation of bodies for dissection.

The results observed are very interesting, knowing that these tests were carried out by injection alone with no tapping.

To obtain optimum preservation of the body, a bronopol concentration of 1% by weight was used for a total injected quantity of 4 liters.

Since the base solution in this particular case was diluted with 3.5 liters and not 5.5 liters of water per 500 ml of solution, the alcohol, glycerine, citrate and eosin concentrations were also increased by a factor of about 1.5.

The results obtained during dissections performed 14 and 16 days after death were very interesting. Moreover, very good results were obtained with regard to the state of preservation of the body and tissue suppleness, the blood being thickened, thus allowing observation and dissection in better conditions. A lack of odour was also noted.

For example, the above-mentioned composition (2) was used on a subject of average build (a man who had been dead for eight days).

Before the test was performed, very marked lividities, large green abdominal marks and sunken eyes (the body had been frozen) were observed.

The product was then injected through the carotid artery in one pass (one times 3.6 liters of water and 400 ml of the above-mentioned composition (2)), for better product dilution (injection total=4 liters) (bronopol concentration=1%).

The subject was moved alternately between the cold storage room (7° C.) and the autopsy table (25° C.).
Result after injection: good fluid flow, placed in cold storage.
Result on day 1: the body was taken out for practical work on the following day. No swelling was observed, only the arms showed significant venous signs, no green abdominal marks.
Result on day 2: practical work carried out—the doctors dissected the neck, the muscles were of a good colour, no odour. The doctor did not observe any difference from a recently deceased body that had not received a formalin injection.

Result on day 6: the doctors removed the heart and lungs which were found to be of good quality. The viscera were well preserved which facilitated removal and gave the internal appearance of a recent, non-"embalmed" body. The blood was thickened.

Additional tests were carried out.

Accordingly, the concentrated solution used was exactly the same as that used for the family presentation procedures and therefore followed the rules stated above for preparation and dilution except that the amount of liquid injected into the body was only 4 liters in total (with no tapping and no cavity injection).

A standard concentrated solution of 72 g of bronopol (composition 3') was therefore used, half a liter thereof being diluted with 3.5 liters of water to obtain a bronopol concentration of 0.9%.

2. Tests were also carried out in the faculty of medicine for organ preservation.

More particularly, tests were carried out to preserve a heart. The results thus obtained for a heart preservation test over eight months showed that the heart had been preserved in excellent conditions.

Dissection of the heart showed that the organ structure had not changed, the valve chords were very well preserved, the tissue was not particularly rigid and the morphology of the heart had been very well preserved.

The heart was preserved by bathing said heart in a solution composed of 200 $cm^3$ of the standard solution for family presentation preservation procedures at 72 grams of bronopol (composition 3') in 10 liters of water.

The bronopol concentration of this solution was 0.15%.

The invention claimed is:

1. An embalming method comprising injecting into the body a composition comprising 2-bromo-2-nitropropane-1,3-diol, wherein said composition comprises from 0.3% to 1.2% by weight of 2-bromo-2-nitropropane-1,3-diol and wherein the composition is injected by arterial injection.

2. The embalming method of claim 1 wherein said composition comprises from 0.3% to 0.6% by weight of 2-bromo-2-nitropropane-1,3-diol.

3. The embalming method of claim 1, wherein the composition comprises 0.6% by weight of 2-bromo-2-nitropropane-1,3-diol.

4. The method of claim 1, wherein the composition also comprises an anticoagulant.

5. The method of claim 1, wherein the composition also comprises a penetrating agent.

6. The method of claim 1, wherein the composition also comprises an antiseptic.

7. The method of claim 1 wherein the composition also comprises a colouring.

8. A composition comprising 2-bromo-2-nitropropane-1,3-diol, an anticoagulant, a penetrating agent, and optionally a coloring, said composition comprising from 0.3% to 1.2% by weight of 2-bromo-2-nitropropane-1,3-diol.

9. A composition consisting of 2-bromo-2-nitropropane-1,3-diol, an anticoagulant, a penetrating agent, an antiseptic and optionally a coloring, said composition consisting of from 0.3% to 1.2% by weight of 2-bromo-2-nitropropane-1,3-diol.

10. The method of claim 6, wherein the antiseptic is selected from the group consisting of methanol and ethanol.

11. The method of claim 6, wherein the antiseptic is present in an amount of from about 2% to about 45% by weight based on the total weight of said composition.

* * * * *